US009572621B2

(12) United States Patent
Livneh

(10) Patent No.: US 9,572,621 B2

(45) Date of Patent: Feb. 21, 2017

(54) SURGICAL JAWS FOR SEALING TISSUE

(75) Inventor: Steve Livneh, Amherstburg (CA)

(73) Assignee: BOVIE MEDICAL CORPORATION, Clearwater, FL (US)

( * ) Notice: Subject to any disclaimer, the term of this patent is extended or adjusted under 35 U.S.C. 154(b) by 1050 days.

(21) Appl. No.: 12/792,201

(22) Filed: Jun. 2, 2010

(65) Prior Publication Data

US 2010/0305564 A1 Dec. 2, 2010

Related U.S. Application Data

(60) Provisional application No. 61/183,124, filed on Jun. 2, 2009.

(51) Int. Cl.

| | |
|---|---|
| ***A61B 18/14*** | (2006.01) |
| *A61B 17/32* | (2006.01) |
| *A61B 17/28* | (2006.01) |
| *A61B 17/29* | (2006.01) |
| *A61B 18/00* | (2006.01) |

(52) U.S. Cl.

CPC .... *A61B 18/1442* (2013.01); *A61B 17/320016* (2013.01); *A61B 18/148* (2013.01); *A61B 2017/2825* (2013.01); *A61B 2017/2933* (2013.01); *A61B 2018/0063* (2013.01); *A61B 2018/00083* (2013.01); *A61B 2018/1412* (2013.01); *A61B 2018/1455* (2013.01); *A61B 2018/1497* (2013.01)

(58) Field of Classification Search

CPC .......................... A61B 18/1447; A61B 18/085

USPC ..................................... 606/51, 52, 206, 207

See application file for complete search history.

(56) References Cited

U.S. PATENT DOCUMENTS

| | | | | |
|---|---|---|---|---|
| 5,226,908 A | | 7/1993 | Yoon | |
| 5,318,589 A | * | 6/1994 | Lichtman | 606/205 |
| 5,443,479 A | | 8/1995 | Bressi, Jr. | |

(Continued)

FOREIGN PATENT DOCUMENTS

| | | |
|---|---|---|
| CN | 201168050 Y | 12/2008 |
| EP | 1433428 A1 | 6/2004 |
| WO | 9507662 A1 | 3/1995 |

OTHER PUBLICATIONS

English language International Search Report for International Application No. PCT/US2010/001607, mailed Aug. 2, 2010; 2 pages.

(Continued)

*Primary Examiner* — Thomas Giuliani

(74) *Attorney, Agent, or Firm* — Gerald E. Hespos; Michael J. Porco; Matthew T. Hespos

(57) ABSTRACT

A surgical tool assembly for use in electrosurgery includes an elongated sheath movable in a longitudinal direction. The assembly includes a pair of jaws, with each jaw having a plurality of teeth for grasping tissue and a support element supporting the plurality of teeth. The support element is disposed partially within the sheath and extends to a distal end disposed outside of the sheath. The support element includes a first portion extending from the distal end and delineating a first region. The support element further includes a second portion extending from the first portion and delineating a second region. The second portion is curved to engage with the sheath such that the jaws move towards one another as the elongated sheath moves towards the distal end. The teeth extend from the first region into the second region.

21 Claims, 4 Drawing Sheets

(56) References Cited

U.S. PATENT DOCUMENTS

| | | | | |
|---|---|---|---|---|
| 5,458,598 | A * | 10/1995 | Feinberg | A61B 18/1445 606/205 |
| 5,499,998 | A | 3/1996 | Meade | |
| 5,507,297 | A | 4/1996 | Slater et al. | |
| 5,603,723 | A | 2/1997 | Aranyi et al. | |
| 5,611,808 | A * | 3/1997 | Hossain | A61B 18/1442 606/167 |
| 5,735,849 | A * | 4/1998 | Baden | A61B 18/1442 606/205 |
| 5,800,449 | A | 9/1998 | Wales | |
| 5,820,630 | A | 10/1998 | Lind | |
| 5,984,939 | A * | 11/1999 | Yoon | A61B 17/12013 606/139 |
| 6,099,550 | A | 8/2000 | Yoon | |
| 6,261,308 | B1 | 7/2001 | Saavedra | |
| 6,270,497 | B1 | 8/2001 | Sekino et al. | |
| 6,419,675 | B1 * | 7/2002 | Gallo, Sr. | 606/46 |
| 6,458,128 | B1 * | 10/2002 | Schulze | 606/50 |
| 6,679,882 | B1 * | 1/2004 | Kornerup | A61B 18/1445 606/46 |
| 7,815,641 | B2 * | 10/2010 | Dodde | A61B 18/1445 606/20 |
| 2003/0191464 | A1 | 10/2003 | Kidooka | |
| 2004/0254573 | A1 | 12/2004 | Dycus et al. | |
| 2005/0124987 | A1 | 6/2005 | Goble | |
| 2005/0165443 | A1 * | 7/2005 | Livneh | A61B 17/29 606/205 |
| 2008/0015566 | A1 | 1/2008 | Livneh | |
| 2008/0154299 | A1 | 6/2008 | Livneh | |
| 2008/0208246 | A1 | 8/2008 | Livneh | |
| 2008/0294159 | A1 * | 11/2008 | Akahoshi | A61B 18/1445 606/41 |
| 2009/0209959 | A1 | 8/2009 | Bartel | |
| 2010/0057081 | A1 * | 3/2010 | Hanna | 606/51 |
| 2010/0292690 | A1 | 11/2010 | Livneh | |

OTHER PUBLICATIONS

Written Opinion for International Application No. PCT/US2010/001607, mailed Aug. 2, 2010; 5 pages.

International Search Report and Written Opinion for International Application No. PCT/US2010/025891, mailed Apr. 29, 2010; 8 pages.

English Translation of Chinese Patent Publication No. CN201168050Y; obtained from http://google.com/patents/CN201168050Y?cl=en; printed on Nov. 28, 2016.

* cited by examiner

SURGICAL JAWS FOR SEALING TISSUE

CROSS REFERENCE TO RELATED APPLICATION

This application claims the benefit of provisional patent application No. 61/183,124, filed Jun. 2, 2009, which is hereby incorporated by reference.

BACKGROUND OF THE INVENTION

1. Field of the Invention

The subject invention relates generally to surgical jaws for grasping and sealing tissue.

2. Description of the Related Art

Surgical tool assemblies for coagulating and cutting tissue, such as blood vessels, have greatly improved modern surgical techniques and are well known in the art. Such tool assemblies typically include a pair of jaws formed of wire for delivering electrical energy to the tissue, as shown in FIG. 2. The jaws each include a plurality of teeth for grasping the tissue and providing the energy to the tissue. A blade is often disposed adjacent to the jaws for cutting the tissue.

Unfortunately, such wire jaws have a short length, thus limiting the length of tissue coagulation. Furthermore, the curvature of the wires, i.e., the “humps” in the wire, commonly results in bulging of the tissue underneath the humps. Moreover, coagulation of the tissue disposed underneath these humps is usually poor and/or not complete.

The subject invention is directed toward these and other deficiencies of the prior art.

BRIEF SUMMARY AND ADVANTAGES

The subject disclosure provides a surgical tool assembly for use in electrosurgery. The assembly includes an elongated sheath movable in a longitudinal direction. A pair of jaws each includes a plurality of teeth for grasping tissue and a support element supporting the plurality of teeth. The support element is disposed partially within the sheath and extends to a distal end disposed outside of the sheath. The support element includes a first portion extending from the distal end and delineating a first region. The support element further includes a second portion extending from the first portion and delineating a second region. The second portion is curved to engage with the sheath such that the jaws move towards one another as the elongated sheath moves towards the distal end. The teeth extend from the first region into the second region.

By extending the teeth into the second region, the performance of the jaws is enhanced. Specifically, the grasping, coagulation, and cutting length is extended over jaw assemblies of the prior art. Furthermore, this extension of the teeth into the second region eliminates the bulging of tissue under one or all of the curvatures of the jaws. This improves overall coagulation of the tissue.

BRIEF DESCRIPTION OF THE DRAWINGS

Other advantages of the disclosed subject matter will be readily appreciated, as the same becomes better understood by reference to the following detailed description when considered in connection with the accompanying drawings wherein.

DETAILED DESCRIPTION

Referring to the Figures, wherein like numerals indicate like parts throughout the several views, a surgical tool assembly 10 for use in electrosurgery is shown herein.

The surgical tool assembly 10 includes a pair of jaws 12*a*, 12*b*, i.e., a first jaw 12*a* and a second jaw 12*b*, for grasping tissue (not shown), such as a blood vessel. In the illustrated embodiments, each jaw 12*a*, 12*b* is movable. However, those skilled in the art realize that the first jaw 12*a* may be fixed while the second jaw 12*b* is movable, or vice-versa. Also in the illustrated embodiment, the first jaw 12*a* and the second jaw 12*b* are arranged as mirror images of one another, i.e., the jaws 12*a*, 12*b* each have the same general design feature. Those skilled in the art realize that a non-symmetrical arrangement of the jaws 12*a*, 12*b* is not always necessary and that one of the jaws 12*a*, 12*b* may have different feature from the other jaw 12.

Figures 1, 2:
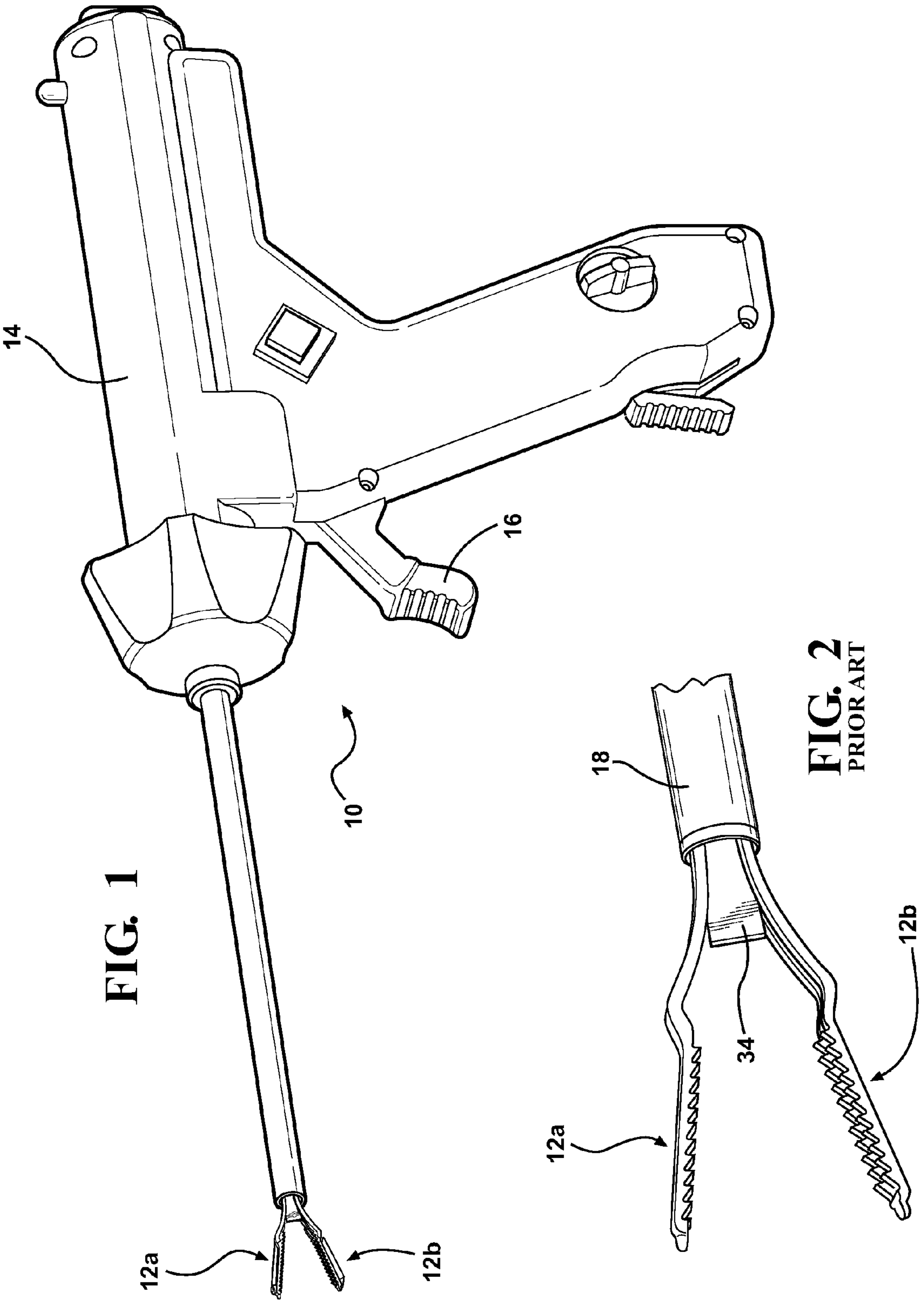
FIG. 1 is a perspective view of a surgical tool assembly including a handle mechanism operatively connected to a pair of jaws.
FIG. 2 is a perspective view of the pair of jaws according to the prior art.

The surgical tool assembly 10 may include a handle mechanism 14 for controlling operation of the jaws 12*a*, 12*b* as well as performing other functions of the assembly 10, as shown in FIG. 1. The handle mechanism 14 of the illustrated embodiment includes a trigger 16 operatively connected to the jaws 12*a*, 12*b*.

Still referring to FIG. 1, the assembly 10 also includes an elongated sheath 18. The elongated sheath 18 of the illustrated embodiment extends away from the handle mechanism 14. The elongated sheath 18 is movable in a longitudinal direction, i.e., back-and-forth along a longitudinal axis (not specifically shown). The elongated sheath 18 is operatively connected to the trigger 16 to control the jaws 12*a*, 12*b*, as will be detailed further herein.

The elongated sheath 18 defines an opening (not numbered). In the illustrated embodiment, the sheath 18 defines a tubular shape, i.e., the sheath 18 has a circular cross section with a hollow interior (not numbered). However, those skilled in the art realize other suitable shapes for the sheath 18 that may be utilized within the scope of the present invention.

The jaws 12*a*, 12*b* each include a plurality of teeth 20 and a support element 22. The teeth 20 are typically utilized for grasping the tissue while the support element 22 supports the teeth 20. The teeth 20 of the illustrated embodiment include a plurality of projections 24 and a plurality of recesses 26 alternating with one another. In the illustrated embodiment, the teeth 20 are serrated, i.e., the projections 24 are pointed.

However, those skilled in the art realize alternative designs to implement the projection 24 and recesses 26.

The support element 22 is disposed partially within the sheath 18. The support element 22 extends to a distal end 28 disposed outside of the sheath 18. In the illustrated embodiment, the support element 22 has a proximal end (not shown) that terminates within the handle mechanism 14.

The support element 22 may be implemented as a rigid wire (not numbered), as best seen in FIGS. 3-6, 8, and 9. Said another way, the support element 22 is generally solid and forms a circular cross section. Of course, other suitable designs for the support element 22 will be realized by those skilled in the art. The support element 22 is preferably formed of an electrically conductive material as discussed further below.

Figure 5:
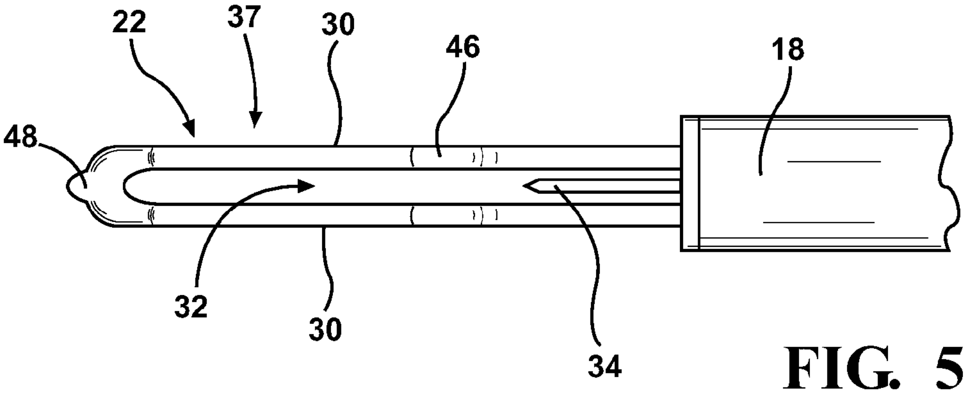
FIG. 5 is a top view of the first embodiment of the pair of jaws.
Figure 6:
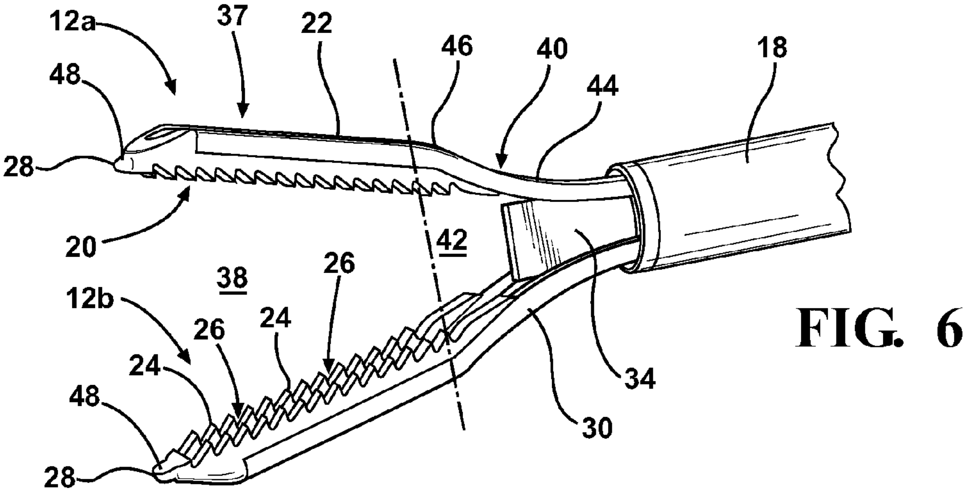
FIG. 6 is a perspective view of a second embodiment of the pair of jaws in an open position.

In the illustrated embodiments, each support element 22 includes a pair of legs 30, as best seen in FIG. 5. The legs 30 are coupled together at the distal end 28. More specifically, in the illustrated embodiments, the legs 30 are formed of a continuous wire which wraps around and changes direction at the distal end 28. Of course, those skilled in the art realize other techniques to implement the legs 30. Furthermore, the support element 22 may be implemented as a single piece (not shown) and not the separate legs 30.

Still referring to FIG. 5, the legs 30 of the illustrated embodiments define a channel 32 therebetween. The assembly 10 of the illustrated embodiments includes a blade 34 movable in the longitudinal direction and disposed in the channel 32. The blade 34 is preferably supported by a wire (not shown) which extends through the sheath 18 and into the handle mechanism 14. As such, the blade 34 may be operated, i.e., moved back and forth, via a lever or trigger (not numbered) on the handle mechanism 14.

Preferably, the jaws 12*a*, 12*b*, especially the teeth 20 and the support element 22, are formed of an electrically conductive material, such as a metal. The jaws 12*a*, 12*b* may be electrically connected to an electrical power source (not shown) for delivering electric current to the tissue. Those skilled in the art realize that the electric current may be delivered as a radio frequency (RF) waveform, as is known to those skilled in the art. The blade 34 is also preferably formed of an electrically conductive material, such as a metal, and may also be electrically connected to the power source. The electrical power source may be connected to a connector (not numbered) disposed on the handle mechanism 14. The electric current is then routed through conductors (not shown) within the handle mechanism 14 and to the support elements 22. The support elements 22 are electrically connected to the teeth 20, such that the electric current may conduct through the teeth 20.

The electric current may be delivered to the tissue using monopolar and/or bipolar techniques, as is well known to those skilled in the art. With the monopolar technique, the electric current is delivered using at least one of the jaws 12*a*, 12*b* and/or the blade. A conductive pad (not shown) in contact with the patient provides a return path for the current. With the bipolar technique, the electric current conducts from the first jaw 12*a* to the second jaw 12*b*, from both jaws 12*a*, 12*b* to the blade 34, or from one of the jaws 12*a*, 12*b* to the blade 34.

Figure 7:
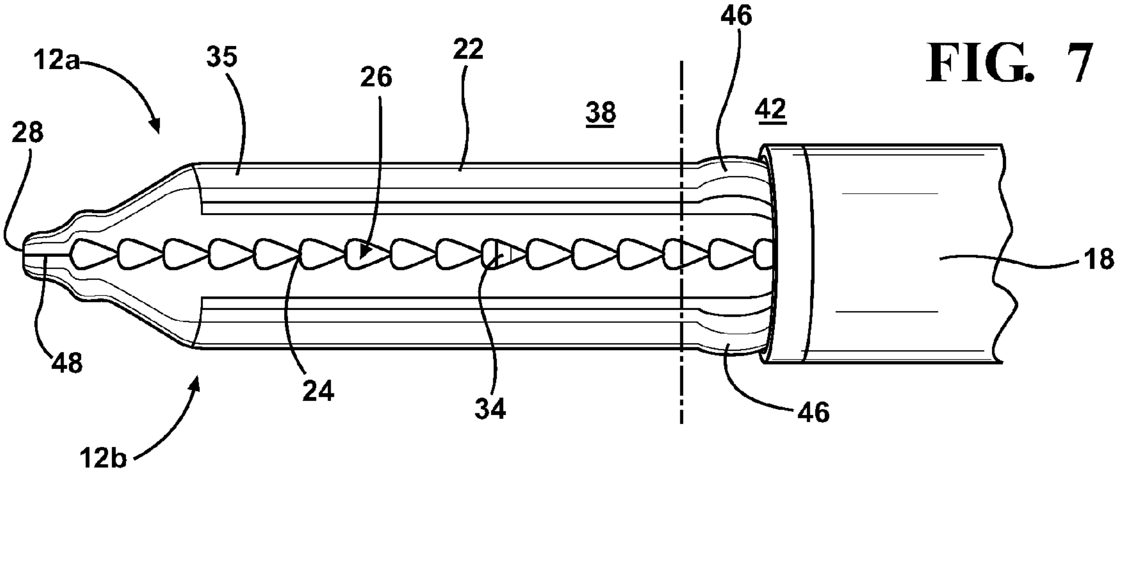
FIG. 7 is a perspective view of the second embodiment of the pair of jaws in a closed position.

In the illustrated embodiments, at least one of the jaws 12*a*, 12*b* is at least partially covered by a non-conductive material 35. Specifically, the non-conductive material may cover at least part of the support element 22 of each jaw 12. However, the non-conductive material does not interrupt the electrical connection between the support element 22 and the teeth 20. In the embodiment shown in FIGS. 6 and 7, the non-conductive material 35 is extending to a point (not numbered) adjacent to the distal end 28 of each jaw 12*a*, 12*b*. As such, the electric current is prevented from flowing from most of the support element 22 to the surrounding tissue. This minimizes the amount of tissue that is exposed to the electric current and provides safety to monopolar applications.

Figure 8:
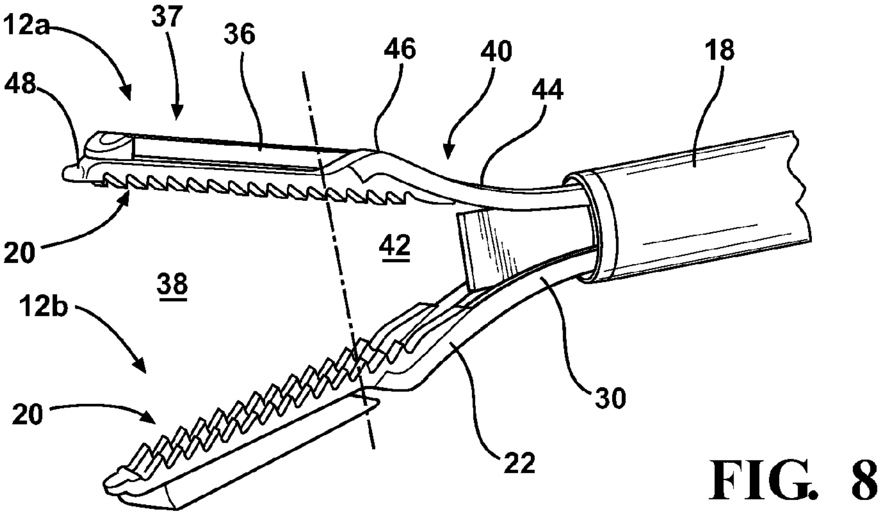
FIG. 8 is a perspective view of a third embodiment of the pair of jaws.
Figure 9:
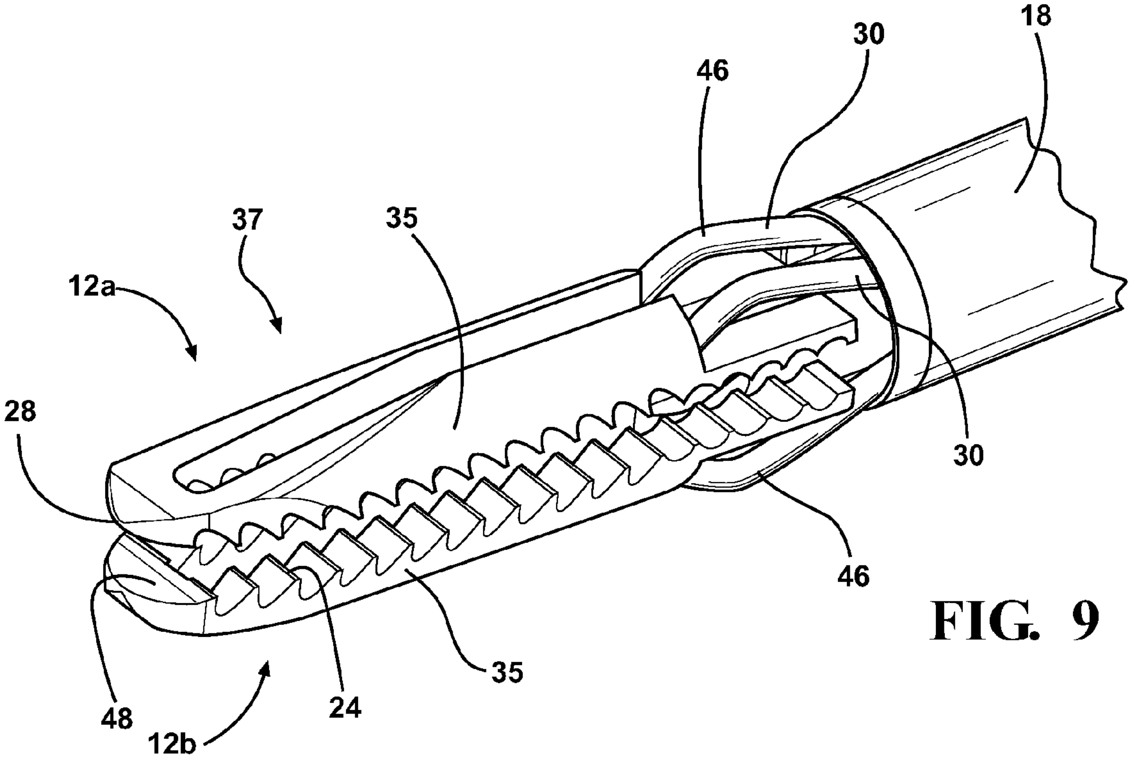
FIG. 9 is a perspective view of a fourth embodiment of the pair of jaws.

The non-conductive material 35 may be a dielectric coating (not separately numbered) that is applied to portions of the jaws 12*a*, 12*b*, as shown in the Figures. An insulated applique 36, as shown in FIG. 8, may also be connected to the support element 22. The applique 36 in the illustrated embodiment is formed of plastic. However, other non-conductive materials may also be suitable, including, but not limited to, ceramics or ceramic plastics.

Figure 3:
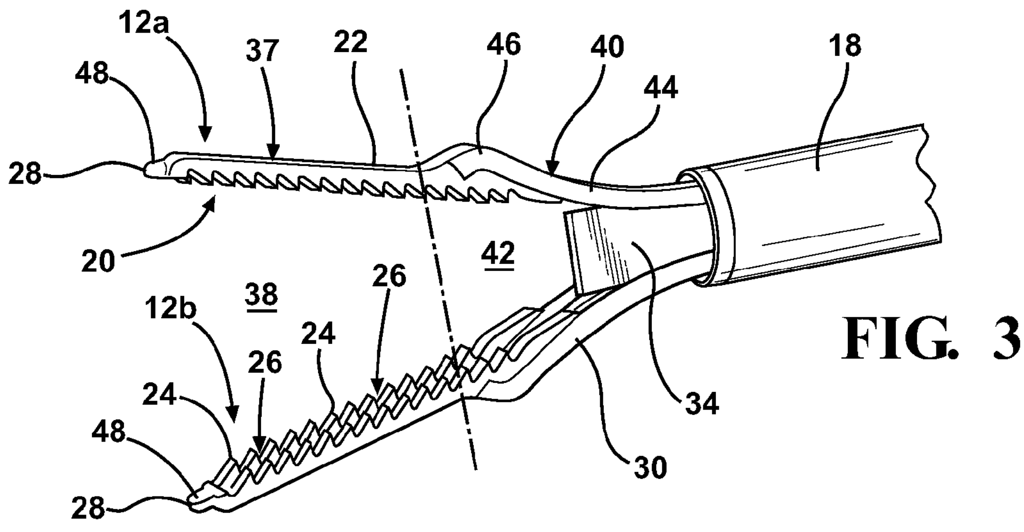
FIG. 3 is a perspective view of a first embodiment of the pair of jaws.
Figure 4:
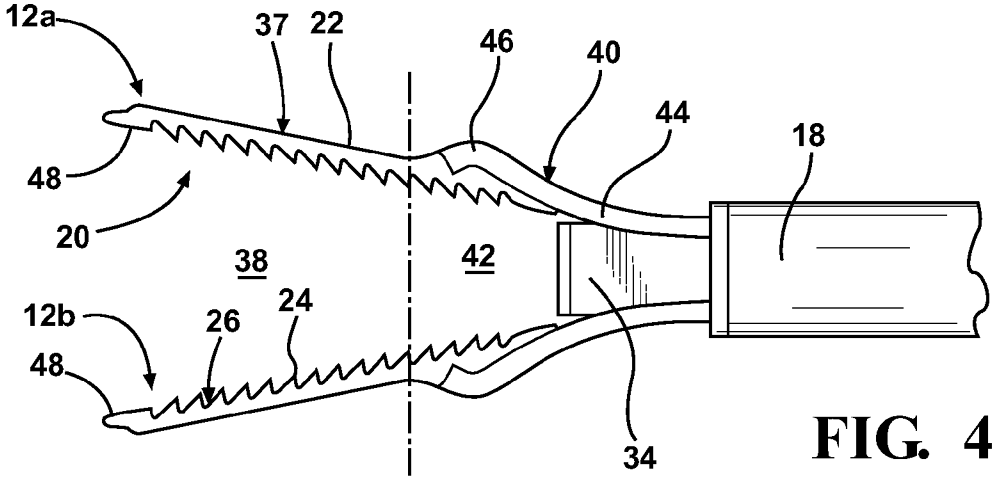
FIG. 4 is a side view of the first embodiment of the pair of jaws.

As best seen with reference to FIGS. 3 and 4, the support element 22 includes a first portion 37 extending to the distal end 28. An area between the first portion 37 of the first jaw 12*a* and the first portion 37 of the second jaw 12*b* delineates a first region 38. The support element 22 also includes a second portion 40 extending to the first portion 37. An area between the second portion 40 of the first jaw 12*a* and the second portion 40 of the second jaw 12*b* delineates a second region 42. Said another way, the regions 38 and 42 are separated, as indicated by the dashed line, by the juncture between a first area between the first portions 37 and a second area between the second portions 40 of the support element 22.

The second portion 40 of the support element 22 is curved to engage with the sheath 18. As such, the back-and-forth movement of the sheath 18 engages with the second portion 40 of the support element 22 and regulates movement of the support elements 22, and accordingly, the jaws 12*a*, 12*b*. More specifically, the curve of the support element 22 is such that the jaws 12*a*, 12*b* move towards one another as the sheath 18 moves towards the distal end 28 of the support element 22.

Even more specifically, in the embodiments shown in FIGS. 3, 4, 6, and 8, the second portion 40 of the jaws 12*a*, 12*b* defines a first curvature 44 and a second curvature 46. The first curvature 44 of the first jaw 12*a* bulges towards the first curvature 44 of the second jaw 12*b*, and vice versa. The first curvature 44 provides a gradual slope which causes a gradual closure of the jaws 12*a*, 12*b* in response to advancement of the sheath 18 toward the distal end 28. The second curvature 46 of the first jaw 12*a* bulges away from the second curvature 46 of the second jaw 12*b*, and vice versa. The second curvature 46 provides a "hump" for providing the final movement of the jaws 12*a*, 12*b* into the closed position as well as rigidity at the end of the movement of the sheath 18.

The teeth 20 are disposed in both the first region 38 and the second region 42. That is, as the teeth 20 are supported at least by the first portion 37 of each jaw of the support element 22, the teeth 20 extend into the first region 38 and the second region 42. Said another way, the teeth 20 are disposed adjacent to at least part of the first portion 37 and at least part of the second portion 40. Said yet another way, the teeth 20 are positioned underneath at least one of the curvatures 44, 46 of the second portion 40 of the first jaw 12*a* in addition to being positioned underneath the first portion 37. Also, the teeth 20 are positioned above at least one of the curvatures 44, 46 of the second portion 40 of the second jaw 12*b* in addition to being positioned above the first portion 37.

By extending the teeth 20 into the second region 42, the performance of the jaws 12*a*, 12*b* is enhanced. Specifically, the grasping, coagulation, and cutting length is extended by approximately 25-35% over jaw assemblies of the prior art. Furthermore, the expansion of the teeth 20 into the second region 42 eliminates the bulging of tissue under one or all of the curvatures 44, 46 that often occurs in prior art jaw assemblies.

In the embodiments shown in FIGS. 3-7, the teeth 20 are attached to both the first and second portions 37, 40 of the support element 22. However, in the embodiment shown in FIG. 9, the teeth 20 are attached only to the first portion 37 of the support element 22, yet extend into the second region 42. As such, in this embodiment, the second portion 40 of the support element 22 retains much of the flexibility of the prior art jaw assemblies.

The assembly 10 may also include tip 48 disposed at the distal end 28 of each of the jaws 12*a*, 12*b*. The tips 48 are disposed to engage one another when the jaws 12*a*, 12*b* are in the closed position. (See FIG. 7.) The tips 48 may prevent the teeth 20 of the first jaw 12*a* from meshing with the teeth 20 of the second jaw 12*b*, and vice versa. That is, the tips 48 may prevent closure of the jaws 12*a*, 12*b* past the closed position.

The present invention has been described herein in an illustrative manner, and it is to be understood that the terminology which has been used is intended to be in the nature of words of description rather than of limitation. Obviously, many modifications and variations of the invention are possible in light of the above teachings. The invention may be practiced otherwise than as specifically described within the scope of the appended claims.

What is claimed is:

1. A surgical tool assembly for use in electrosurgery, the surgical tool assembly comprising: a handle mechanism; an elongated tubular sheath having a circular cross-section and a hollow interior, the elongated tubular sheath being moveable with respect to the handle mechanism in a longitudinal direction; a first jaw including a first wire element and a first set of teeth, the first wire element including a first portion and a second portion, wherein the first portion of the first wire element is curved and extends from the hollow interior of the elongated tubular sheath and a proximal end of the second portion of the first wire element extends from a distal end of the first portion of the first wire element; a second jaw including a second wire element and a second set of teeth, the second wire element including a first portion and a second portion, wherein the first portion of the second wire element is curved and extends from the hollow interior of the elongated tubular sheath and a proximal end of the second portion of the second wire element extends from a distal end of the first portion of the second wire element, the first portion of the first wire element and the first portion of the second wire element bulging away from each other; wherein the first set of teeth includes a first distal portion and a second proximal portion, the first wire element rigidly attaches to the first set of teeth only at the second portion of the first wire element and the first distal portion of the first set of teeth, the second set of teeth includes a first distal portion and a second proximal portion, the second wire element rigidly attaches to the second set of teeth only at the second portion of the second wire element and the first distal portion of the second set of teeth; and wherein, when moved away from the handle mechanism, a distal end of the elongated tubular sheath engages first portions of the first and second wire elements, causing the first and second jaws to move into a closed position.

2. The surgical tool assembly of claim 1, wherein, when the first and second jaws are in the closed position, the position of the first and second sets of teeth with respect to the distal end of the elongated tubular sheath is such that tissue of a patient is prevented from bulging between the distal end of the elongated tubular sheath and the first and second sets of teeth.

3. The surgical tool assembly of claim 1, wherein, when the first and second jaws are in the closed position, the second proximal portion of the first set of teeth and second proximal portion of the second set of teeth extend at least halfway through an area between the first portion of the first wire element and the second portion of the second wire element.

4. The surgical tool assembly of claim 3, wherein when the first and second jaws are in the closed position, the first and second sets of teeth are positioned at least along a range of positions in the longitudinal direction from at least halfway through an area between the first portion of the first wire element and the first portion of the second wire element to a distal end of the second portions of the first and second wire elements.

5. The surgical tool assembly of claim 1, wherein the first and second wire elements are configured as solid wires having a substantially circular cross-section.

6. The surgical tool assembly of claim 1, wherein the first jaw and second jaw are complementary and are configured to clamp tissue of a patient.

7. The surgical tool assembly of claim 1, wherein the first wire element includes a first pair of legs and the second wire element includes a second pair of legs, and wherein the first pair of legs is coupled together at a distal end of the first wire element and the second pair of legs is coupled together at a distal end of the second wire element.

8. The surgical tool assembly of claim 7, wherein, when the first and second jaws are in the closed position, a channel is formed between the legs of the first pair of legs and between the legs of the second pair of legs.

9. The surgical tool assembly of claim 8, further comprising a blade moveable in the longitudinal direction within the channel.

10. The surgical tool assembly of claim 1, wherein at least one of the first and second jaws is formed of an electrically conductive material.

11. The surgical tool assembly of claim 10, wherein the at least one of the first and second jaws is electrically connected to an electrical power source for delivering electrical power to tissue of a patient.

12. The surgical tool assembly of claim 10, wherein the at least one of the first and second jaws is at least partially covered by a non-conductive material.

13. The surgical tool assembly of claim 1, wherein, the first jaw includes a first tip disposed on a distal end of the first jaw and the second jaw includes a second tip disposed on a distal end of the second jaw, the first tip and the second tip each including a flat surface, such that, when the first and second jaws are in the closed position, the flat surface of the first tip and the flat surface of the second tip engage each other to prevent the first set of teeth and the second set of teeth from meshing together.

14. A surgical tool assembly comprising: an elongated tubular sheath having a circular cross-section and a hollow interior, the elongated tubular sheath being moveable in a longitudinal direction; a first jaw including a first wire element and a first set of teeth, the first wire element including a first portion and a second portion, wherein the first portion of the first wire element is curved and extends from the hollow interior of the elongated tubular sheath and a proximal end of the second portion of the first wire element extends from a distal end of the first portion of the first wire element; a second jaw including a second wire element and a second set of teeth, the second wire element including a first portion and a second portion, wherein the first portion of the second wire element is curved and extends from the hollow interior of the elongated tubular sheath and a proximal end of the second portion of the second wire element extends from a distal end of the first portion of the second wire element, the first portion of the first wire element and the first portion of the second wire element bulging away from each other; and wherein the first set of teeth includes a first distal portion and a second proximal portion, the first wire element rigidly attaches to the first set of teeth only at the second portion of the first wire element and the first distal portion of the first set of teeth, the second set of teeth includes a first distal portion and a second proximal portion, the second wire element rigidly attaches to the second set of teeth only at the second portion of the second wire element and the first distal portion of the second set of teeth.

15. The surgical tool assembly of claim 14, further comprising a blade moveable in the longitudinal direction, wherein the first wire element includes a first pair of legs defining a first channel, wherein the second wire element includes a second pair of legs defining a second channel, and wherein the blade is moveable within the first and second channels.

16. The surgical tool assembly of claim 14, wherein at least one of the first and second jaws is formed of an electrically conductive material and is connected to an electrical power source for delivering electrical power to tissue of a patient.

17. The surgical tool assembly of claim 14, wherein when the elongated tubular sheath is moved in a distal longitudinal direction, a distal end of the elongated tubular sheath engages the first portion of the first wire element and the first portion of the second wire element to force the first and second jaws into a closed position.

18. The surgical tool assembly of claim 17, wherein, when the first and second jaws are in the closed position, the second proximal portion of the first set of teeth and the second proximal portion of the second set of teeth extend at least halfway through an area between the first portion of the first wire element and the first portion of the second wire element.

19. The surgical tool assembly of claim 18, wherein, when the first and second jaws are in the closed position, the position of the first and second sets of teeth with respect to the distal end of the elongated tubular sheath is such that tissue of a patient is prevented from bulging between the distal end of the elongated tubular sheath and the first and second sets of teeth.

20. The surgical tool assembly of claim 17, wherein when the first and second jaws are in the closed position, the first and second sets of teeth are positioned at least along a range of positions in the longitudinal direction from at least halfway through an area between the first portion of the first wire element and the first portion of the second wire element to a distal end of the second portions of the first and second wire elements.

21. The surgical tool assembly of claim 17, wherein, the first jaw includes a first tip disposed on a distal end of the first jaw and the second jaw includes a second tip disposed on a distal end of the second jaw, the first tip and the second tip each including a flat surface, such that, when the first and second jaws are in the closed position, the flat surface of the first tip and the flat surface of the second tip engage each other to prevent the first set of teeth and the second set of teeth from meshing together.

* * * * *